(12) United States Patent
Babich

(10) Patent No.: US 12,307,798 B2
(45) Date of Patent: May 20, 2025

(54) SYSTEM AND METHOD FOR AUTOMATED PROCESSING OF ELECTRONIC RECORDS WITH MACHINE LEARNING MODELS

(71) Applicant: Mitchell International, Inc., San Diego, CA (US)

(72) Inventor: John Babich, San Diego, CA (US)

(73) Assignee: Mitchell International, Inc., San Diego, CA (US)

(*) Notice: Subject to any disclaimer, the term of this patent is extended or adjusted under 35 U.S.C. 154(b) by 944 days.

(21) Appl. No.: 17/408,311

(22) Filed: Aug. 20, 2021

(65) Prior Publication Data

US 2023/0060099 A1 Feb. 23, 2023

(51) Int. Cl.
| | |
|---|---|
| *G06N 20/00* | (2019.01) |
| *G06F 18/214* | (2023.01) |
| *G06F 18/2433* | (2023.01) |
| *G06V 30/412* | (2022.01) |

(52) U.S. Cl.
CPC .......... *G06V 30/412* (2022.01); *G06F 18/214* (2023.01); *G06F 18/2433* (2023.01); *G06N 20/00* (2019.01)

(58) Field of Classification Search
CPC . G06V 30/412; G06F 18/214; G06F 18/2433; G06N 20/00; G06N 3/08; G06N 5/01; G06N 5/046; G06N 20/20; G16H 10/60; G16H 15/00
See application file for complete search history.

(56) References Cited

U.S. PATENT DOCUMENTS

| | | | | |
|---|---|---|---|---|
| 10,140,636 | B2 * | 11/2018 | Pepper | G06Q 30/04 |
| 11,315,196 | B1 * | 4/2022 | Narayan | G06F 18/2193 |
| 2011/0246262 | A1 * | 10/2011 | Pepper | G06Q 40/12 |
| | | | | 706/54 |
| 2020/0052973 | A1 * | 2/2020 | Forte | H04L 41/12 |

(Continued)

OTHER PUBLICATIONS

Baumel, Tal, et al. "Multi-label classification of patient notes: case study on ICD code assignment." Workshops at the thirty-second AAAI conference on artificial intelligence. 2018 (Year: 2018).*

(Continued)

*Primary Examiner* — Andrew T Mcintosh
(74) *Attorney, Agent, or Firm* — Sheridan Ross P.C.

(57) ABSTRACT

In general, one aspect disclosed features a system, comprising: a hardware processor; and a non-transitory machine-readable storage medium encoded with instructions executable by the hardware processor to perform operations comprising: receiving an electronic record, the electronic record representing a medical bill, the medical bill comprising a plurality of attributes; mapping each attribute in the medical bill to a single bucket of a predetermined second quantity of the buckets according to a predetermined correspondence between the attributes and the buckets, the first quantity exceeding the second quantity; and providing identifiers of the single buckets as input to a machine learning model, the machine learning model being trained according to historical correspondences between the buckets and decisions of whether human review was necessary, wherein responsive to the input, the machine learning model provides as output an indication of whether the medical bill should be reviewed by a human.

20 Claims, 10 Drawing Sheets

Bill No. 602

Binary Vectors 704

| | | | | | | | | | | | | | | | | | | |
|---|---|---|---|---|---|---|---|---|---|---|---|---|---|---|---|---|---|---|
| 1034 | 0 | 0 | 0 | 0 | 0 | 0 | 0 | 1 | 0 | 0 | 0 | 1 | 0 | 0 | 0 | 0 | 1 | 1 | 0 |
| 1037 | 0 | 0 | 0 | 0 | 0 | 0 | 0 | 1 | 0 | 0 | 0 | 0 | 0 | 0 | 0 | 0 | 0 | 0 | 0 |

(56) References Cited

U.S. PATENT DOCUMENTS

2020/0211120 A1* 7/2020 Wang ............... G06Q 40/08
2020/0411146 A1* 12/2020 McEwing ........... G16H 50/70

OTHER PUBLICATIONS

Li, Yue, et al. "Inferring multimodal latent topics from electronic health records." Nature communications 11.1 (2020): 2536 (Year: 2020).*

Shamitha, S. Kotekani, and Velchamy Ilango. "A time-efficient model for detecting fraudulent health insurance claims using Artificial neural networks." 2020 International Conference on System, Computation, Automation and Networking (ICSCAN). IEEE, 2020 (Year: 2020).*

* cited by examiner

| Bill No. 602 | Diagnostic Codes 604 |
|---|---|
| 1034 | I70.90, M54.2, R51, S09.90XA, S16.1XXA, V49.88XA, Y92.410 |
| 1037 | M25.531 |

FIG. 6

| Bill No. 602 | Binary Vectors 704 |
|---|---|
| 1034 | 0 0 0 0 0 0 0 0 1 0 0 0 1 0 0 0 0 0 1 1 0 |
| 1037 | 0 0 0 0 0 0 0 0 1 0 0 0 0 0 0 0 0 0 0 0 0 |

FIG. 7

ND METHOD FOR AUTOMATED
PROCESSING OF ELECTRONIC RECORDS
WITH MACHINE LEARNING MODELS

DESCRIPTION OF RELATED ART

The disclosed technology relates generally to automated processing of electronic records, and more particularly some embodiments relate to the application of machine learning models to such processing.

SUMMARY

In general, one aspect disclosed features a system, comprising: a hardware processor; and a non-transitory machine-readable storage medium encoded with instructions executable by the hardware processor to perform operations comprising: receiving an electronic record, the electronic record representing a medical bill, the medical bill comprising a plurality of attributes; mapping each attribute in the medical bill to a single bucket of a predetermined second quantity of the buckets according to a predetermined correspondence between the attributes and the buckets, the first quantity exceeding the second quantity; and providing identifiers of the single buckets as input to a machine learning model, the machine learning model being trained according to historical correspondences between the buckets and decisions of whether human review was necessary, wherein responsive to the input, the machine learning model provides as output an indication of whether the medical bill should be reviewed by a human.

Embodiments of the system may include one or more of the following features. In some embodiments, providing the identifiers of the single buckets as input to the machine learning model comprises: providing an identifier of a particular bucket as input to the machine learning model only once for the medical bill. In some embodiments, the operations further comprise applying the output of the machine learning model as input to one or more predetermined rules; and determining whether the medical bill should be reviewed by a human based on output of the one or more predetermined rules. In some embodiments, the operations further comprise the attributes comprise at least one code, each code being either a procedure code or a diagnostic code; and the predetermined correspondence between the codes and the buckets is based on categories established by at least one health organization. In some embodiments, the attributes comprise procedure codes; and the predetermined correspondence between the procedure codes and the buckets is based on categories established by the American Medical Association. In some embodiments, the attributes comprise diagnostic codes; and the predetermined correspondence between the diagnostic codes and the buckets is based on categories established by the World Health Organization. In some embodiments, the operations further comprise generating a vector of binary numbers, wherein: each position in the vector represents one of the buckets, a first value of the binary numbers indicates an attribute of the medical bill was mapped to the corresponding bucket, and a second value of the binary numbers indicates no attribute of the medical bill was mapped to the corresponding bucket; and providing identifiers of the single buckets as input to a machine learning model comprises providing the vector of binary numbers as input to a machine learning model.

In general, one aspect disclosed features a non-transitory machine-readable storage medium encoded with instructions executable by a hardware processor of a computing component, the machine-readable storage medium comprising instructions to cause the hardware processor to perform operations comprising: receiving an electronic record, the electronic record representing a medical bill, the medical bill comprising a plurality of attributes; mapping each attribute in the medical bill to a single bucket of a predetermined second quantity of the buckets according to a predetermined correspondence between the attributes and the buckets, the first quantity exceeding the second quantity; and providing identifiers of the single buckets as input to a machine learning model, the machine learning model being trained according to historical correspondences between the buckets and decisions of whether human review was necessary, wherein responsive to the input, the machine learning model provides as output an indication of whether the medical bill should be reviewed by a human.

Embodiments of the non-transitory machine-readable storage medium may include one or more of the following features. In some embodiments, providing the identifiers of the single buckets as input to the machine learning model comprises: providing an identifier of a particular bucket as input to the machine learning model only once for the medical bill. In some embodiments, the operations further comprise applying the output of the machine learning model as input to one or more predetermined rules; and determining whether the medical bill should be reviewed by a human based on output of the one or more predetermined rules. In some embodiments, the attributes comprise at least one code, each code being either a procedure code or a diagnostic code; and the predetermined correspondence between the codes and the buckets is based on categories established by at least one health organization. In some embodiments, the attributes comprise procedure codes; and the predetermined correspondence between the procedure codes and the buckets is based on categories established by the American Medical Association. In some embodiments, the attributes comprise diagnostic codes; and the predetermined correspondence between the diagnostic codes and the buckets is based on categories established by the World Health Organization. In some embodiments, the operations further comprise generating a vector of binary numbers, wherein: each position in the vector represents one of the buckets, a first value of the binary numbers indicates an attribute of the medical bill was mapped to the corresponding bucket, and a second value of the binary numbers indicates no attribute of the medical bill was mapped to the corresponding bucket; and providing identifiers of the single buckets as input to a machine learning model comprises providing the vector of binary numbers as input to a machine learning model.

In general, one aspect disclosed features a computer-implemented method, comprising: receiving an electronic record, the electronic record representing a medical bill, the medical bill comprising a plurality of attributes; mapping each attribute in the medical bill to a single bucket of a predetermined second quantity of the buckets according to a predetermined correspondence between the attributes and the buckets, the first quantity exceeding the second quantity; and providing identifiers of the single buckets as input to a machine learning model, the machine learning model being trained according to historical correspondences between the buckets and decisions of whether human review was necessary, wherein responsive to the input, the machine learning model provides as output an indication of whether the medical bill should be reviewed by a human.

Embodiments of the method may include one or more of the following features. In some embodiments, providing the identifiers of the single buckets as input to the machine learning model comprises: providing an identifier of a particular bucket as input to the machine learning model only once for the medical bill. Some embodiments comprise applying the output of the machine learning model as input to one or more predetermined rules; and determining whether the medical bill should be reviewed by a human based on output of the one or more predetermined rules. In some embodiments, the attributes comprise at least one code, each code being either a procedure code or a diagnostic code; and the predetermined correspondence between the codes and the buckets is based on categories established by at least one health organization. In some embodiments, the attributes comprise procedure codes; the predetermined correspondence between the procedure codes and the buckets is based on categories established by the American Medical Association; the attributes comprise diagnostic codes; and the predetermined correspondence between the diagnostic codes and the buckets is based on categories established by the World Health Organization. Some embodiments comprise generating a vector of binary numbers, wherein: each position in the vector represents one of the buckets, a first value of the binary numbers indicates an attribute of the medical bill was mapped to the corresponding bucket, and a second value of the binary numbers indicates no attribute of the medical bill was mapped to the corresponding bucket; and providing identifiers of the single buckets as input to a machine learning model comprises providing the vector of binary numbers as input to a machine learning model.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 4 illustrates an example medical bill.

FIG. 5 illustrates another example medical bill.

FIG. 6 illustrates portions of two example medical bills.

FIG. 7 illustrates example binary input vectors for the medical bills of FIG. 6.

The figures are not exhaustive and do not limit the present disclosure to the precise form disclosed.

DETAILED DESCRIPTION

Interactions between complex computing systems increasingly involve the exchange and processing of electronic records. For example, medical bill provider computing systems generate electronic records representing medical bills, and transmit the electronic records to bill processing computing systems. The bill processing computing systems process the bills, and transmit electronic records representing the processed bills to bill consumer computing systems. But currently considerable human interaction is required to review and adjust each of the processed bills before transmission to the bill consumer computing systems.

The disclosed technology is described in terms of processing medical bills. However, the disclosed technology may be applied to processing other types of bills. For example, the disclosed technology may be applied to processing automobile repair bills and similar bills. The disclosed technology may be applied to other sorts of documents that currently require human review.

Figure 1:
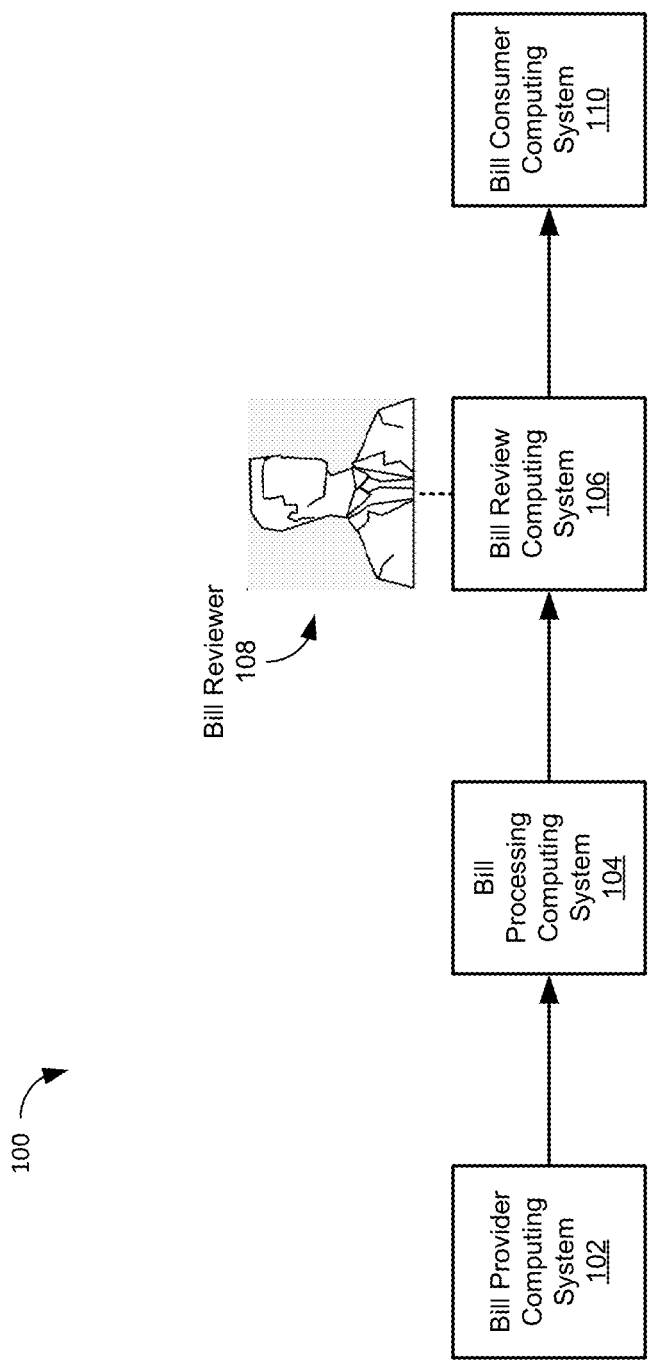
FIG. 1 depicts a prior art medical billing system.

FIG. 1 depicts a prior art medical billing system 100. In system 100, medical bills are generated by a bill provider computing system 102. Electronic records representing the medical bills are transmitted to a bill processing computing system 104. After processing, electronic records representing the processed bills are transmitted to a bill review computing system 106, where each bill is reviewed, and possibly adjusted, by a human bill reviewer 108. After human review, electronic records representing the reviewed medical bills are transmitted to a bill consumer computing system 110.

The human review process suffers from several disadvantages. First, human review is time-consuming, and therefore increases the time required to deliver the bills to the end user, the bill consumer. Second, while human review serves to correct some errors in the bills, it is imperfect, and often overlooks some errors while introducing others. Accordingly, it is desirable to reduce the need for human review to improve the speed and accuracy of the bill processing.

Figure 2:
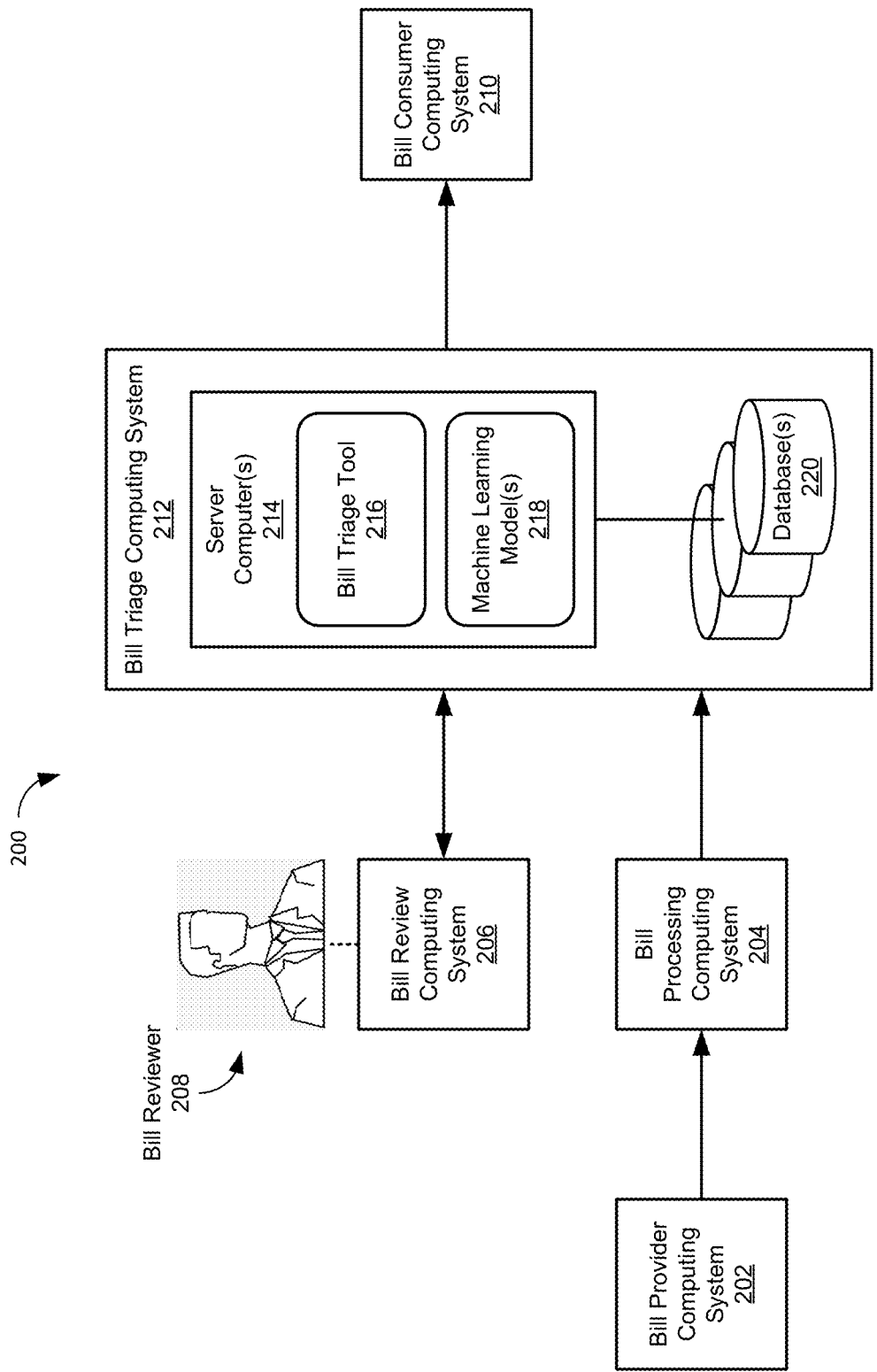
FIG. 2 depicts an improved medical billing system according to some embodiments of the disclosed technologies.

FIG. 2 depicts an improved medical billing system 200 according to some embodiments of the disclosed technologies. Referring to FIG. 2, the medical billing system 200 may include a bill provider computing system 202, a bill processing computing system 206, a bill triage computing system 212, a bill review computing system 206, and a bill consumer computing system 210. The computing systems described herein may be implemented as described below with reference to FIG. 10. Furthermore, while the computing systems are depicted in a particular arrangement in FIG. 2, other arrangements are contemplated. For example, certain computing systems may be combined, divided into multiple computing systems, or any combination thereof. As one example, the bill provider computing system 202 may be combined with the bill provider computing system 210, and may be operated by a single entity, such as an insurance carrier.

The bill provider computing system 202 generates medical bills. The bill provider computing system 202 may be implemented, for example, as an Electronic Data Interchange (EDI) System, or a similar system. The bill provider computing system 202 may be operated by an insurance carrier or payer. The bill provider computing system 202 may generate electronic records representing the medical bills, and may transmit those electronic records to the bill processing computing system 204. The transmission of electronic records described herein may be implemented by any means. For example, the electronic records may be transmitted over one or electronic computing networks, which may include the Internet.

The bill processing computing system 204 may automatically process each bill to determine whether the bill should be disqualified or rejected or whether the associated fee is accurate or should be adjusted, for example according to factors such as jurisdictional regulations, proprietary edits, industry standard practices, correct coding, provider fraud, duplicate checks, billing errors, other payment calculations, and the like. The medical bills may be workers compensation or auto casualty medical bills, for example, although other types of bills may be submitted for review as well.

The medical billing system 200 may include a bill triage computing system 212. The bill triage computing system 212 may include one or more server computers 214. The server computers 214 may host a bill triage tool 216 and one or more machine learning models 218. The bill triage tool 216 and machine learning models 218 may be implemented as one or more software packages executing on the server computers 214. The medical billing system 200 may include one or more databases 220. The databases 220 may store processing rules and other data.

After automated processing of the bills, the bill processing computing system 204 may transmit electronic records representing the processed medical bills to the bill triage computing system 212. The bill triage tool 216 may process each medical bill to determine whether human review is required. This processing may include modifying the structure of the data in the bill to enable the use of the machine learning models 218. The modified data may be applied as input to the trained machine learning models 218. The training of the machine learning models is discussed below. Responsive to this input, the machine learning models 218 may output data indicating whether human review of the bill is required. The bill triage tool 216 may process this output data using one or more rules stored in the databases 220 to determine whether human review is required.

When human review of a bill is required, the bill triage computing system 212 transmits an electronic record representing the bill to the bill review computing system 206 for review by a human bill reviewer 208. After review and possible adjustment of the bill, the bill review computing system 206 may transmit an electronic record representing the bill to the bill consumer computing system 210, either directly or via one or more of the other computing systems.

The improved medical billing system 200 of FIG. 2 may provide one or more advantages over conventional medical billing systems. For example, the improved medical billing system 200 may significantly reduce the need for human review of the medical bills by automatically determining whether human review is needed. When human review is not needed for a medical bill, human review is completely eliminated, thereby increasing the speed and accuracy of the system. This "straight through" or "zero touch" processing is facilitated by the disclosed use of machine learning models, and can improve efficiency and cost savings for insurance carriers and other users.

Figure 3:
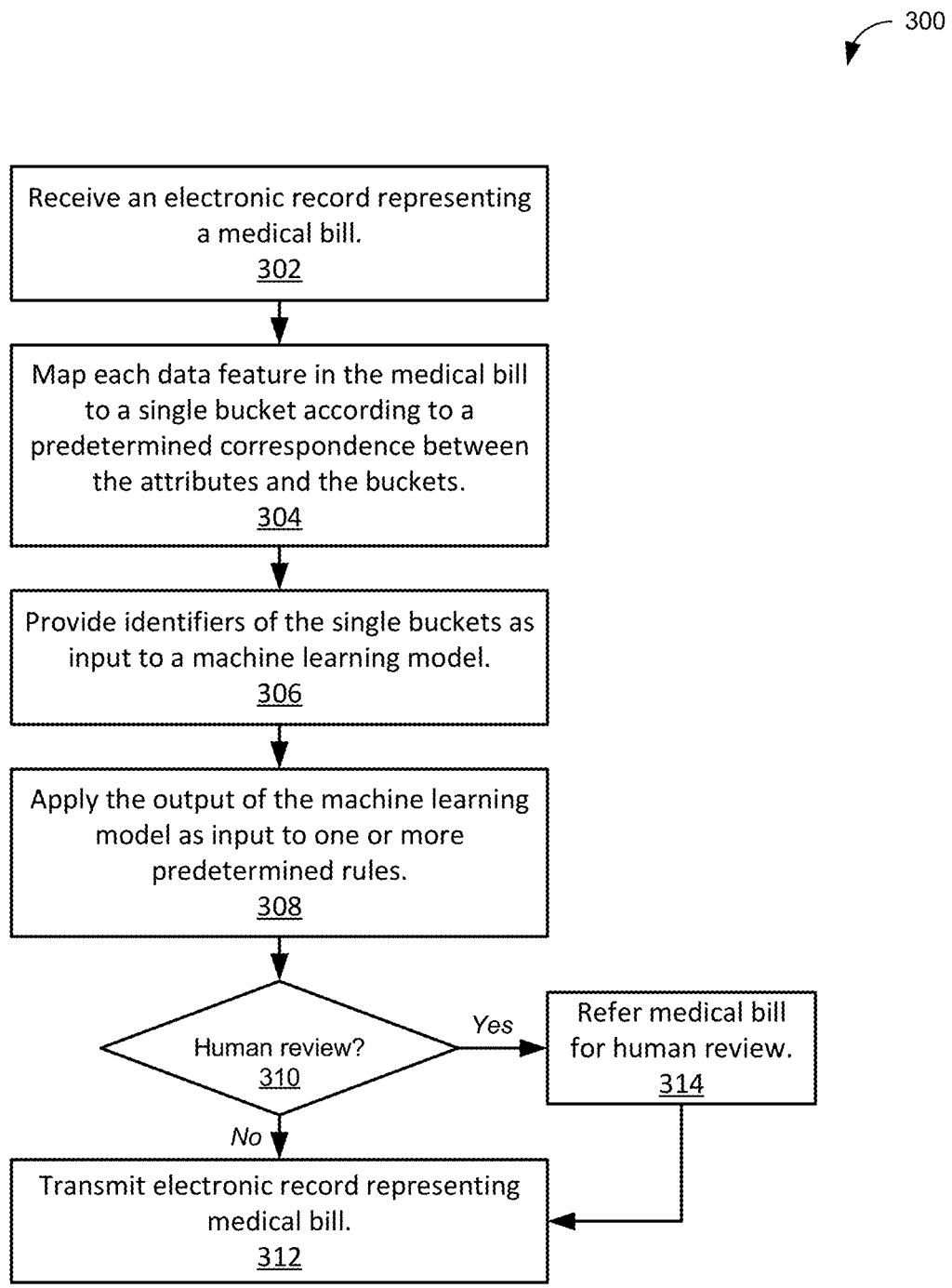
FIG. 3 is a flowchart illustrating a process for automated processing of electronic records with machine learning models according to some embodiments of the disclosed technologies.

FIG. 3 is a flowchart illustrating a process 300 for automated processing of electronic records with machine learning models according to some embodiments of the disclosed technologies. For example, the process 300 may be implemented in the improved medical billing system 200 of FIG. 2.

The elements of the process 300 are presented in one arrangement. However, it should be understood that one or more elements of the process may be performed in a different order, in parallel, omitted entirely, and the like. Furthermore, the process 300 may include other elements in addition to those presented. For example, the process 300 may include error-handling functions if exceptions occur, and the like.

Referring to FIG. 3, the process 300 may include receiving an electronic record representing a medical bill, at 302. In the example of FIG. 2, the bill triage computing system 212 may receive the electronic record. The medical bill may include a plurality of attributes. The attributes may include any features of the bill. For example, the attributes may include codes such as procedure codes and diagnostic codes. The attributes may include costs such as amounts charged, deductibles, and coverage limits. The attributes may include insurance coverage type, for example describing whether the coverage is for workers compensation, auto casualty, and similar coverage types. The attributes may describe other features of the bill, for example such as the state of jurisdiction, the zip code of the provider, and similar features.

Figure 4:
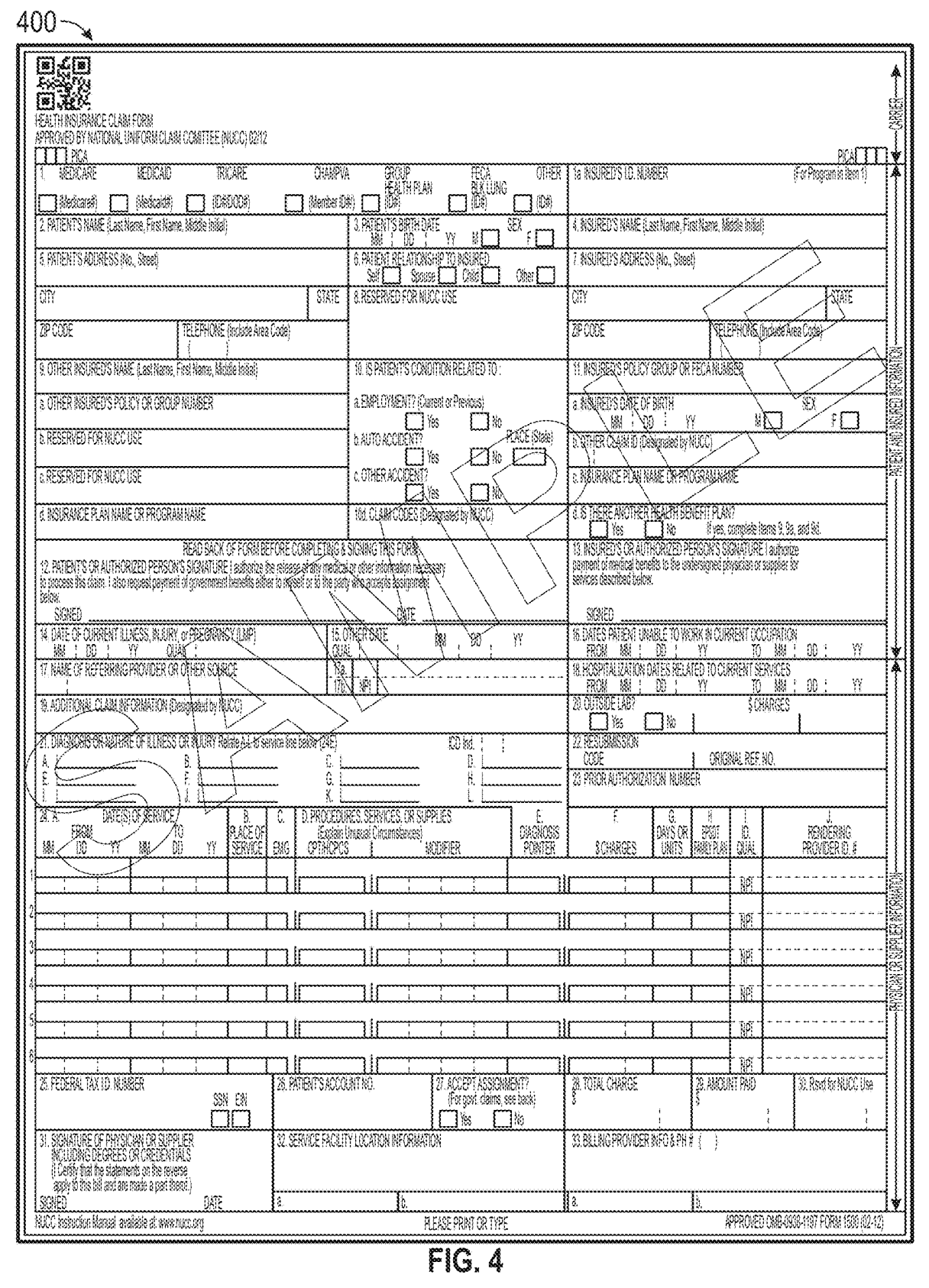

FIG. 4 illustrates an example medical bill 400. The format and contents of medical bills are often tightly controlled by applicable legal rules and regulations. In the example of FIG. 4, the medical bill 400 is a CMS-1500 Health Insurance Claim Form approved by the National Uniform Claim Committee (NUCC). Note in this example, the text fields of the medical bill 400 are blank, but in practice the medical bill 400 would be populated with attributes.

Figure 5:
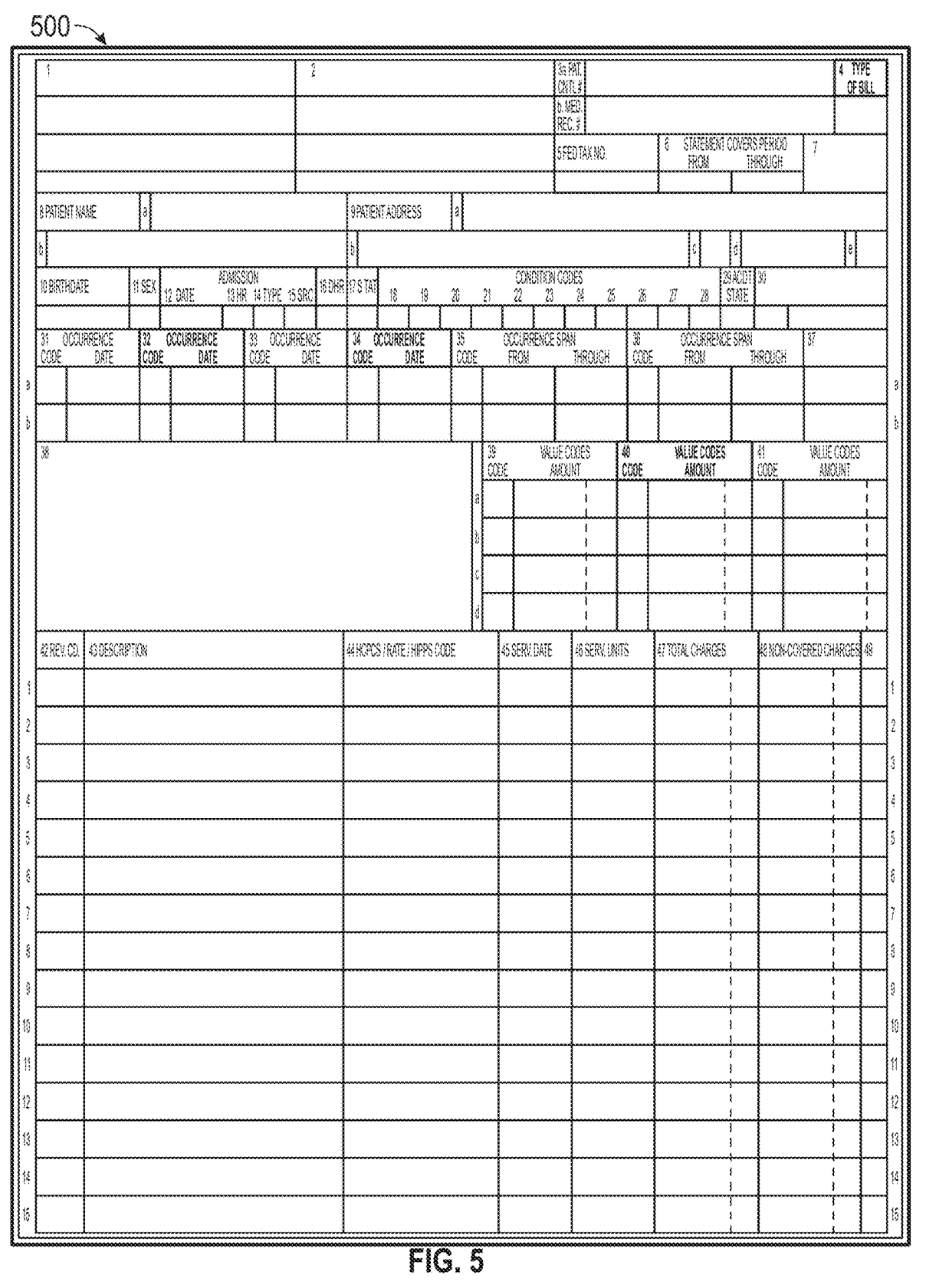
Figure 5:
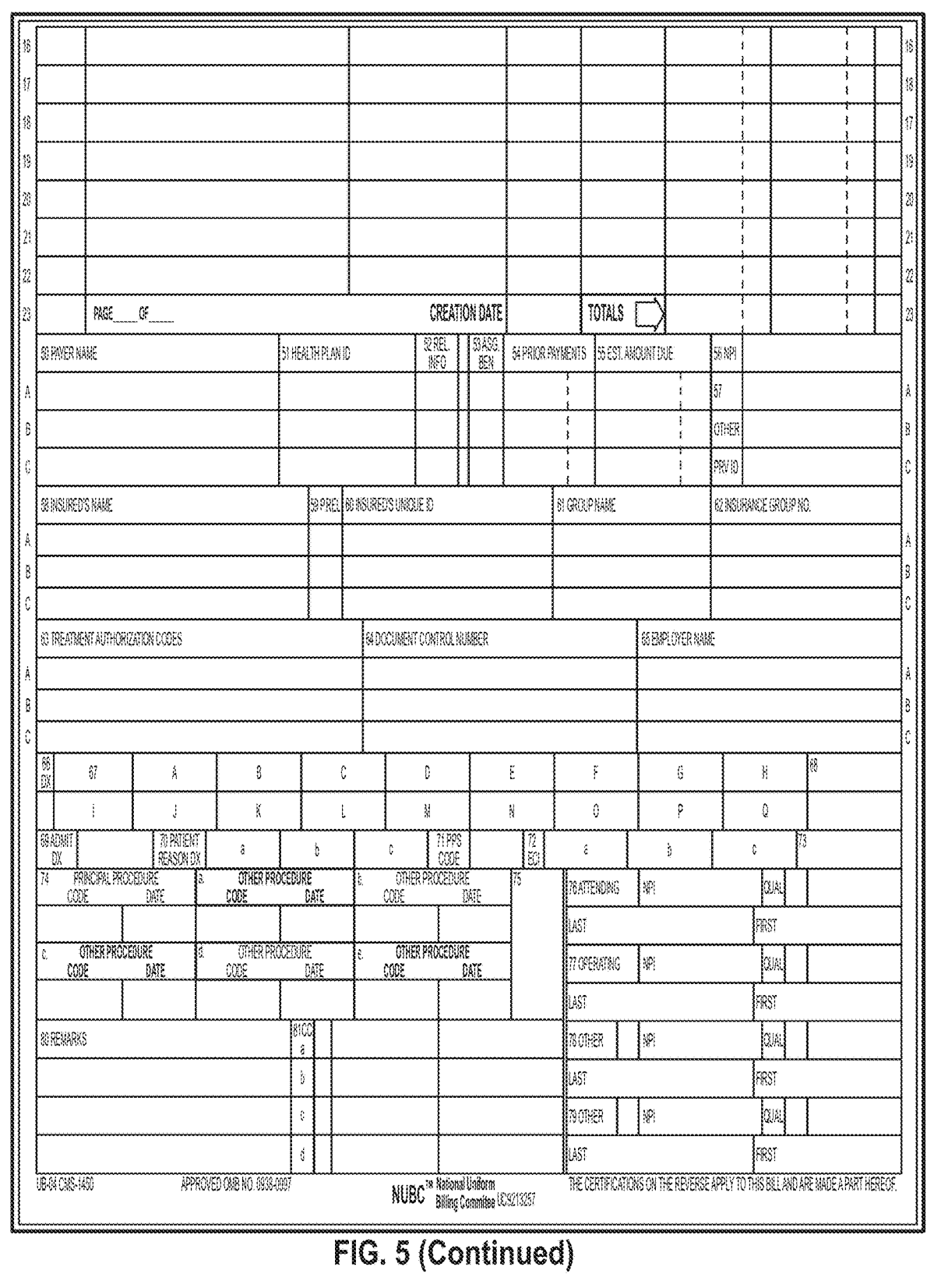

FIG. 5 illustrates another example medical bill 500. In the example of FIG. 5, the medical bill 500 is a UB-04 CMS-1450 Health Insurance Claim Form licensed from the National Uniform Billing Committee (NUBC). Note in this example, the text fields of the medical bill 500 are blank, but in practice the medical bill 500 would be populated with attributes.

The number of possible attributes of a medical bill is vast. For example, the number of existing procedure codes and diagnosis codes exceed 70,000 and 69,000, respectively, yielding millions of possible combinations. It is difficult to apply current machine learning techniques to process such a large number of possibilities. Furthermore, the number of criteria vary significantly, as bills may contain hundreds of lines or just a few lines. In addition, the number of diagnosis codes may vary. The disclosed technology solves these problems by mapping the attributes to a much smaller number of possible values, referred to herein as "buckets". The mapping may encapsulate millions of combinations into a smaller number of inputs that accurately reflect those combinations. In one embodiment, only 300 buckets are used.

Referring again to FIG. 3, the process 300 may include mapping each attribute in the medical bill to a single bucket according to a predetermined correspondence between the attribute and the buckets, at 304. For example, the predetermined correspondences between the buckets and codes such as diagnostic and procedure codes may be based on categories established by at least one health organization. In some embodiments, the predetermined correspondence between procedure codes and the buckets may be based on categories established by the American Medical Association. In some embodiments, the predetermined correspondence between the diagnostic codes and the buckets may be based on categories established by the World Health Organization. In the example of FIG. 2, the bill triage tool 216 may perform the mapping, and the predetermined correspondences may be stored in the databases 220.

Referring again to FIG. 3, the process 300 may include providing identifiers of the single buckets as input to a machine learning model, at 306. In the example of FIG. 2, the bill triage tool 216 may provide the identifiers to one or more of the machine learning models 218. Any machine learning models may be used. For example, the machine learning models and techniques may include decision trees, neural networks, gradient boosting, and similar machine learning models and techniques. The machine learning models may be trained previously according to historical correspondences between the buckets and decisions of whether human review was necessary. The training may be supervised, unsupervised, or a combination thereof, and may continue between operations for the lifetime of the system.

In some embodiments, providing identifiers of the single buckets for a medical bill as input to a machine learning model may include providing a vector of binary numbers as input to the machine learning model. Each position in the vector represents one of the buckets. One value of a binary number indicates an attribute of the medical bill was mapped to the corresponding bucket, while the other value of the binary number indicates no attribute of the medical bill was mapped to the corresponding bucket.

FIG. 6 illustrates portions of two example medical bills. Referring to FIG. 6, each bill is identified by a bill number, at 602, and lists one or more diagnostic codes, at 604.

FIG. 7 illustrates example binary input vectors for the medical bills of FIG. 6. Referring to FIG. 7, each bill is identified by its bill number, at 602, and has a binary vector, at 704. For clarity, only 21 bucket positions are shown in each vector 704. In practice, a larger number of vectors may be used.

In the example of FIGS. 6 and 7, each bit position corresponds to one of the buckets. A value of "1" indicates an attribute corresponding to that bucket appeared in the medical bill. A value of "0" indicates no attribute corresponding to that bucket appeared in the medical bill.

In some embodiments, an identifier of a particular bucket is input to the machine learning model only once for a medical bill, regardless of how many times (exceeding zero) an attribute corresponding to the bucket appeared in the medical bill.

In the example of FIGS. 6 and 7, it can be seen that the seven diagnostic codes of bill number 1034 have been mapped to four buckets, while the one diagnostic code in bill number 1037 has been mapped to only one bucket.

Returning to the process 300 of FIG. 3, responsive to the input, the machine learning model provides as output an indication of whether the medical bill should be reviewed by a human. In some embodiments, the output provides a confidence score that indicates the likelihood that the bill should be reviewed by a human. For example, the confidence score may be a value between 0 and 1. The closer the value is to 1, the higher the confidence. Carriers may specify the level of confidence required to indicate no human review is needed. For example, a carrier may select a confidence threshold. When the confidence score for a bill exceeds the threshold, the system may indicate no human review of that bill is required. In this manner, each carrier may tune the system to fit their specific use case.

The output may be applied as a flag to the electronic document representing the corresponding medical bill. In some embodiments, the medical bill may be provided for human review responsive to the indication. In some embodiments, the output of the machine learning model may be provided as input to one or more predetermined rules, at 308, and the decision whether to refer the medical bill for human review may be based on the output of the one or more predetermined rules.

The output may be used to drive automated workflows. In the example of FIG. 3, when human review is not needed, at 310, the process 300 may include transmitting an electronic record representing the processed medical record, at 312. In the example of FIG. 2, the electronic record may be transmitted to the bill consumer computing system 210. Alternatively, when human review is needed, at 310, the process 300 may include referring the medical bill for human review, at 314. Following human review, an electronic record representing the processed medical record may be transmitted, at 316, for example as described above.

Figure 8:
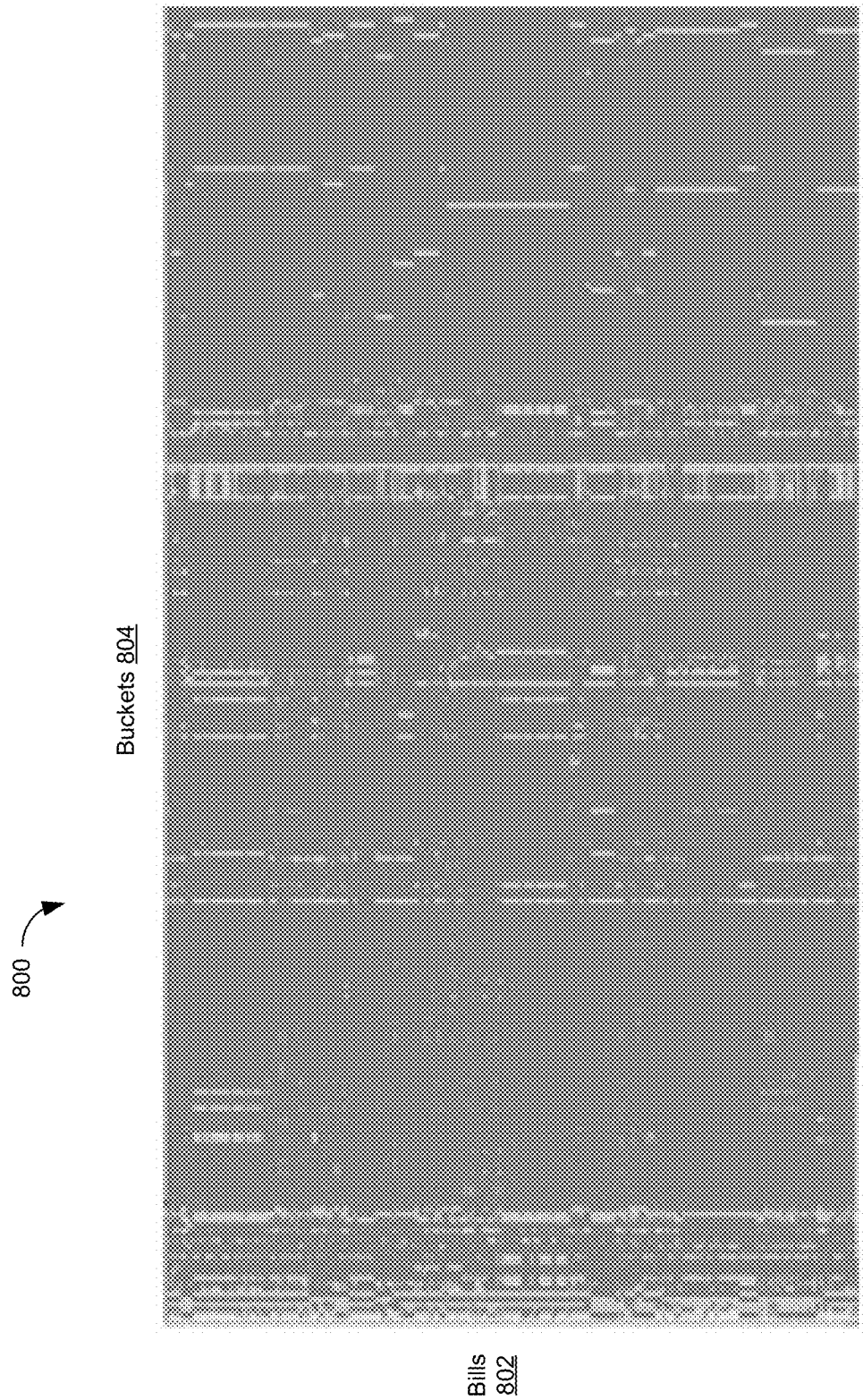
FIG. 8 is a graphical representation of a portion of raw binary input data for training the machine learning models according to some embodiments of the disclosed technologies.

FIG. 8 is a graphical representation 800 of a portion of raw binary input data for training the machine learning models according to some embodiments of the disclosed technologies. Each row represents a bill 802. Each column represents a bucket 804. In the graphical representation 800, each light-colored dot represents a binary "1", indicating an attribute mapped to the corresponding bucket appeared in the corresponding bill. Each dark-colored dot represents a binary "0", indicating no attribute mapped to the corresponding bucket appeared in the corresponding bill. Patterns are clearly visible in graphical representation 800, indicating the transformed data is quite suitable for machine learning.

Figure 9:
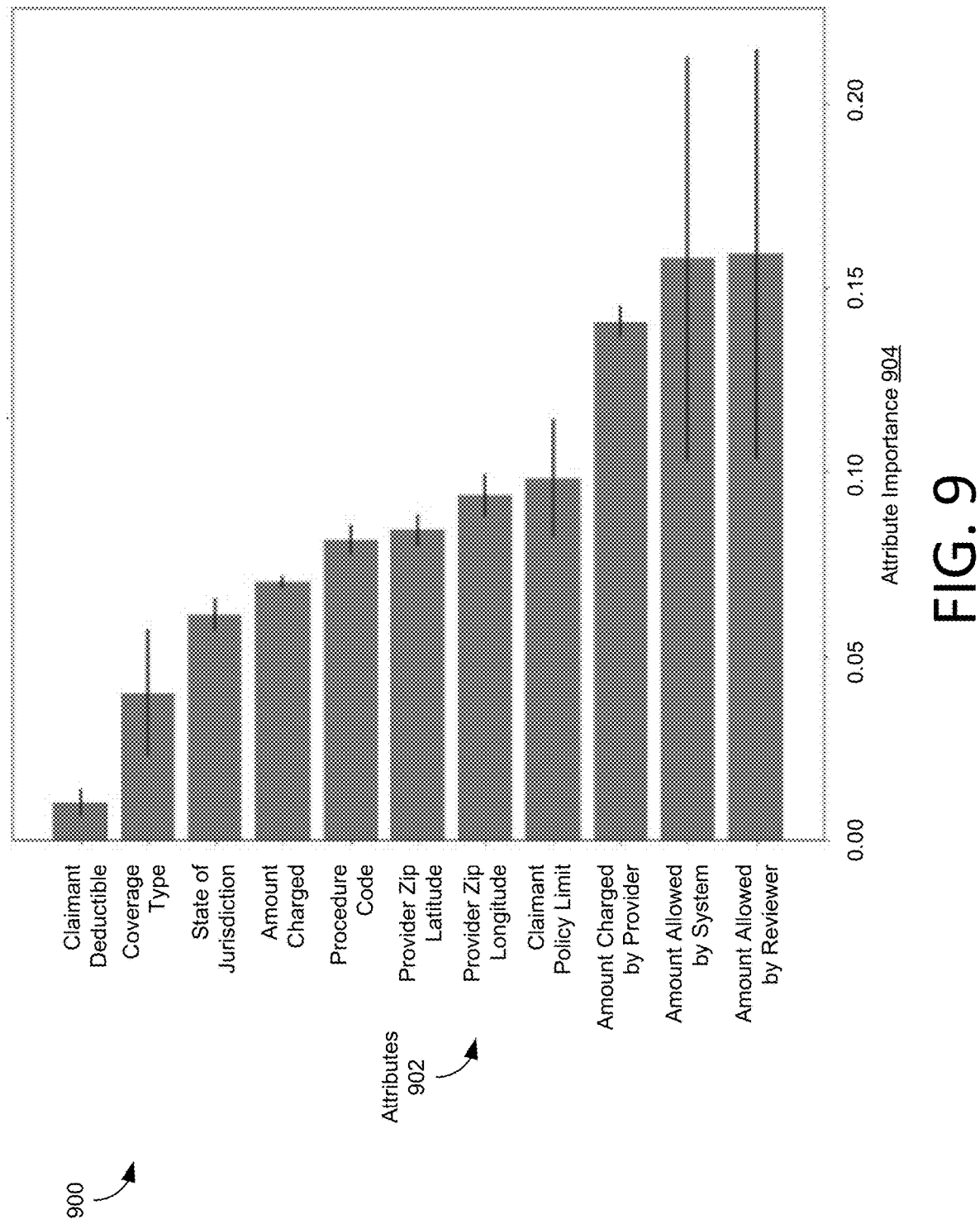
FIG. 9 is a graphical representation of an analysis of example outputs of a trained machine learning model using gradient boosting according to some embodiments of the disclosed technologies.

FIG. 9 is a graphical representation 900 of an analysis of example outputs of a trained machine learning model using gradient boosting according to some embodiments of the disclosed technologies. A number of example attributes of the processed medical bills are shown at 902. The depicted features are claimant deductible, coverage type, state of jurisdiction, amount charged, procedure code, provider zip code of latitude and longitude, policy limit for the claimant (e.g., policyholder), amount charged by the provider, amount allowed by the bill processing system, and amount as revised by a human reviewer.

The importance of each attribute is shown at 904. A large attribute importance number indicates the feature was statistically important, and therefore the system was able to deduce the outcome by considering it. From the graphical representation 900 it is clear that the most important attributes involve amounts charged and allowed. This feature could reflect a human bias in the training data toward referring expensive bills for human review. In some embodiments, some or all attributes related to cost may be omitted from the training data, the input data during regular use, or both. These embodiments may serve to mitigate any human bias concerning cost. However, customers may automatically review high dollar bills as a policy, regardless of the output of the models.

The disclosed technology may automatically determine whether human review is needed for medical bills. The disclosed technology may provide other insights as well. For example, these insights may include whether to pay a medical bill, whether the medical bill is one of a kind bill, whether the medical bill is the first of its type, and whether the medical bill is one of many of the same type.

Levels of expertise vary among the human reviewers. The disclosed use of machine-learning models may focus exclusively on outcomes related to the most experienced adjusters, and then effectively share this knowledge with new and inexperienced ones. The models may also be aggregated from the industry to provide a number of views to the human adjusters. For example, the views may include industry aggregate, carrier level, adjuster aggregate, and similar views.

The disclosed technology possesses substantial advantages over the status quo in process outcomes. Current systems are partially implemented through explicit business rule logic. In contrast, the disclosed technology minimizes the need to write, test, and deploy explicit business rule logic. The disclosed technology achieves higher straight-through processing rates (i.e., without human review) than is otherwise feasible based on discrete rule sets. The disclosed technology also offers the opportunity to continually improve the accuracy of the automation through direct feedback into the machine learning model(s).

The disclosed technology also possesses substantial advantages over the status quo in business outcomes. The disclosed technology reduces the number of bills that humans need to review, thereby saving costs associated with manual tasks, improving consistency and accuracy, optimizing cycle time, payment, and escalations, and freeing human adjusters to perform other customer service tasks.

Figure 10:
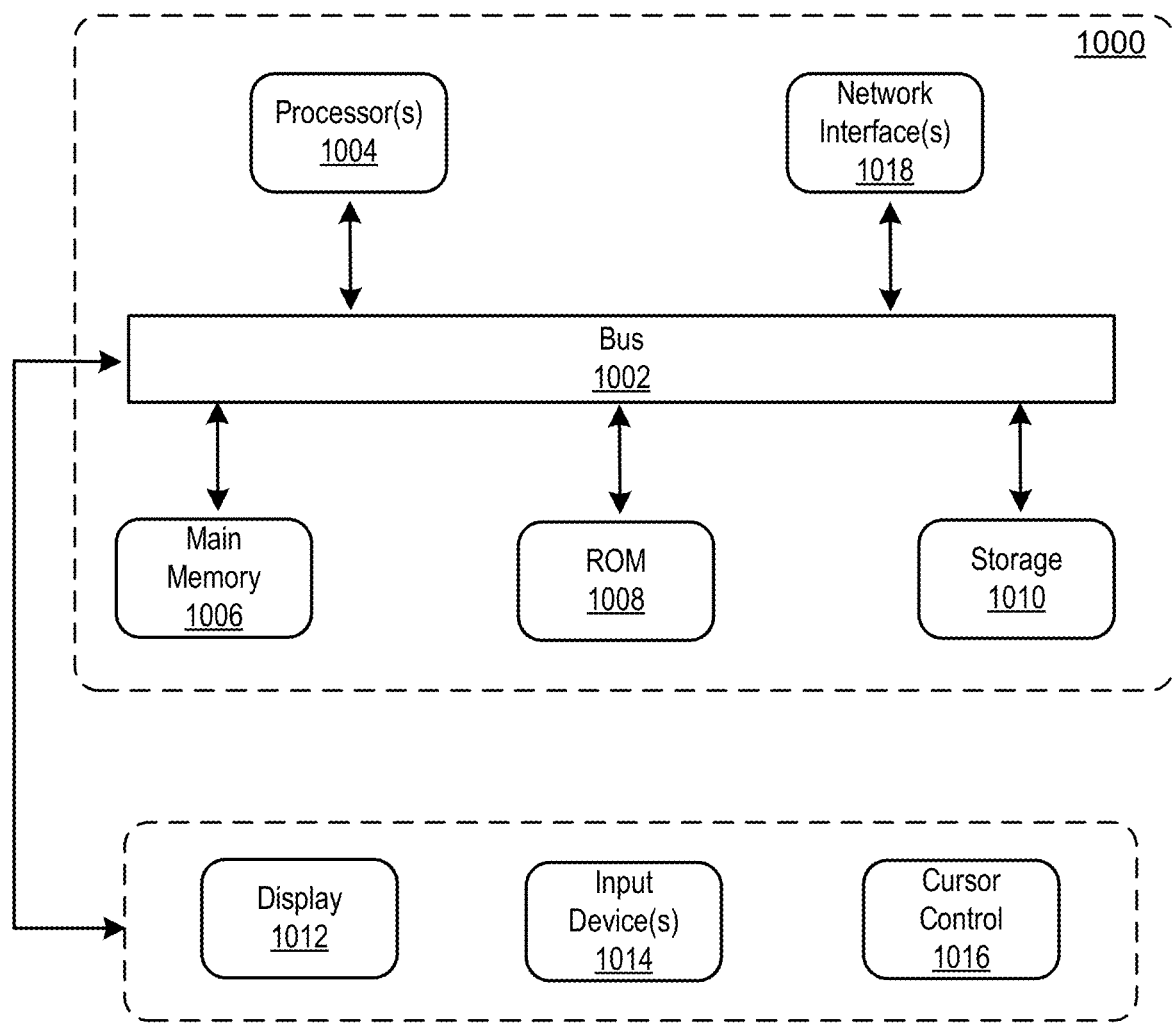
FIG. 10 is an example computing component that may be used to implement various features of embodiments described in the present disclosure.

FIG. 10 depicts a block diagram of an example computer system 1000 in which embodiments described herein may be implemented. The computer system 1000 includes a bus 1002 or other communication mechanism for communicating information, one or more hardware processors 1004 coupled with bus 1002 for processing information. Hardware processor(s) 1004 may be, for example, one or more general purpose microprocessors.

The computer system 1000 also includes a main memory 1006, such as a random access memory (RAM), cache and/or other dynamic storage devices, coupled to bus 1002 for storing information and instructions to be executed by processor 1004. Main memory 1006 also may be used for storing temporary variables or other intermediate information during execution of instructions to be executed by processor 1004. Such instructions, when stored in storage media accessible to processor 1004, render computer system 1000 into a special-purpose machine that is customized to perform the operations specified in the instructions.

The computer system 1000 further includes a read only memory (ROM) 1008 or other static storage device coupled to bus 1002 for storing static information and instructions for processor 1004. A storage device 1010, such as a magnetic disk, optical disk, or USB thumb drive (Flash drive), etc., is provided and coupled to bus 1002 for storing information and instructions.

The computer system 1000 may be coupled via bus 1002 to a display 1012, such as a liquid crystal display (LCD) (or touch screen), for displaying information to a computer user. An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. In some embodiments, the same direction information and command selections as cursor control may be implemented via receiving touches on a touch screen without a cursor.

The computing system 1000 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1000 may implement the techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor(s) 1004 executing one or more sequences of one or more instructions contained in main memory 1006. Such instructions may be read into main memory 1006 from another storage medium, such as storage device 1010. Execution of the sequences of instructions contained in main memory 1006 causes processor(s) 1004 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1010. Volatile media includes dynamic memory, such as main memory 1006. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1002. Transmission media can also take the form of acoustic or light waves, such as those generated during radio-wave and infra-red data communications.

The computer system 1000 also includes a communication interface 1018 coupled to bus 1002. Network interface 1018 provides a two-way data communication coupling to one or more network links that are connected to one or more local networks. For example, communication interface 1018 may be an integrated services digital network (ISDN) card, cable modem, satellite modem, or a modem to provide a data communication connection to a corresponding type of telephone line. As another example, network interface 1018 may be a local area network (LAN) card to provide a data communication connection to a compatible LAN (or a WAN component to communicate with a WAN). Wireless links may also be implemented. In any such implementation, network interface 1018 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 1018, which carry the digital data to and from computer system 1000, are example forms of transmission media.

The computer system 1000 can send messages and receive data, including program code, through the network(s), network link and communication interface 1018. In the Internet example, a server might transmit a requested code for an application program through the Internet, the ISP, the local network and the communication interface 1018.

The received code may be executed by processor 1004 as it is received, and/or stored in storage device 1010, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1000.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this record, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A system, comprising:
    a hardware processor; and
    a non-transitory machine-readable storage medium encoded with instructions executable by the hardware processor to perform operations comprising:
        receiving an electronic record, the electronic record representing a medical bill, the medical bill comprising a plurality of attributes;
        mapping each attribute in the medical bill to a single bucket of a plurality of buckets according to a predetermined correspondence between the attributes and the buckets;
        generating an identifier for each of the single buckets to which attributes in the medical bill were mapped, wherein each identifier comprises a vector of binary number and wherein each position in the vector represents one or the buckets; and
        providing the identifiers of each of the single buckets to which attributes in the medical bill were mapped as input to a machine learning model, the machine learning model being trained according to historical correspondences between the buckets and decisions of whether human review was necessary, wherein responsive to the input, the machine learning model provides as output an indication of whether the medical bill should be reviewed by a human.

2. The system of claim 1, wherein providing the identifiers of the single buckets as input to the machine learning model comprises:
    providing an identifier of a particular bucket as input to the machine learning model only once for the medical bill.

3. The system of claim 1, the operations further comprising:
applying the output of the machine learning model as input to one or more predetermined rules; and
determining whether the medical bill should be reviewed by a human based on output of the one or more predetermined rules.

4. The system of claim 1, wherein:
the attributes comprise at least one code, each code being either a procedure code or a diagnostic code; and
the predetermined correspondence between the codes and the buckets is based on categories established by at least one health organization.

5. The system of claim 1, wherein:
the attributes comprise procedure codes; and
the predetermined correspondence between the procedure codes and the buckets is based on categories established by the American Medical Association.

6. The system of claim 1, wherein:
the attributes comprise diagnostic codes; and
the predetermined correspondence between the diagnostic codes and the buckets is based on categories established by the World Health Organization.

7. The system of claim 1, wherein:
a first value of the binary numbers indicates an attribute of the medical bill was mapped to the corresponding bucket, and
a second value of the binary numbers indicates no attribute of the medical bill was mapped to the corresponding bucket; and
providing identifiers of the single buckets as input to a machine learning model comprises providing the vector of binary numbers as input to a machine learning model.

8. A non-transitory machine-readable storage medium encoded with instructions executable by a hardware processor of a computing component, the machine-readable storage medium comprising instructions to cause the hardware processor to perform operations comprising:
receiving an electronic record, the electronic record representing a medical bill, the medical bill comprising a plurality of attributes;
mapping each attribute in the medical bill to a single bucket of a plurality of buckets according to a predetermined correspondence between the attributes and the buckets;
generating an identifier for each of the single buckets to which attributes in the medical bill were mapped, wherein each identifier comprises a vector of binary number and wherein each position in the vector represents one or the buckets; and
providing the identifiers of each of the single buckets to which attributes in the medical bill were mapped as input to a machine learning model, the machine learning model being trained according to historical correspondences between the buckets and decisions of whether human review was necessary, wherein responsive to the input, the machine learning model provides as output an indication of whether the medical bill should be reviewed by a human.

9. The non-transitory machine-readable storage medium of claim 8, wherein providing the identifiers of the single buckets as input to the machine learning model comprises:
providing an identifier of a particular bucket as input to the machine learning model only once for the medical bill.

10. The non-transitory machine-readable storage medium of claim 8, the operations further comprising:
applying the output of the machine learning model as input to one or more predetermined rules; and
determining whether the medical bill should be reviewed by a human based on output of the one or more predetermined rules.

11. The non-transitory machine-readable storage medium of claim 8, wherein:
the attributes comprise at least one code, each code being either a procedure code or a diagnostic code; and
the predetermined correspondence between the codes and the buckets is based on categories established by at least one health organization.

12. The non-transitory machine-readable storage medium of claim 8, wherein:
the attributes comprise procedure codes; and
the predetermined correspondence between the procedure codes and the buckets is based on categories established by the American Medical Association.

13. The non-transitory machine-readable storage medium of claim 8, wherein:
the attributes comprise diagnostic codes; and
the predetermined correspondence between the diagnostic codes and the buckets is based on categories established by the World Health Organization.

14. The non-transitory machine-readable storage medium of claim 8,
wherein:
a first value of the binary numbers indicates an attribute of the medical bill was mapped to the corresponding bucket, and
a second value of the binary numbers indicates no attribute of the medical bill was mapped to the corresponding bucket; and
providing identifiers of the single buckets as input to a machine learning model comprises providing the vector of binary numbers as input to a machine learning model.

15. A computer-implemented method, comprising:
receiving an electronic record, the electronic record representing a medical bill, the medical bill comprising a plurality of attributes;
mapping each attribute in the medical bill to a single bucket of a plurality of buckets according to a predetermined correspondence between the attributes and the buckets;
generating an identifier for each of the single buckets to which attributes in the medical bill were mapped, wherein each identifier comprises a vector of binary number and wherein each position in the vector represents one or the buckets; and
providing the identifiers of each of the single buckets to which attributes in the medical bill were mapped as input to a machine learning model, the machine learning model being trained according to historical correspondences between the buckets and decisions of whether human review was necessary, wherein responsive to the input, the machine learning model provides as output an indication of whether the medical bill should be reviewed by a human.

16. The computer-implemented method of claim 15, wherein providing the identifiers of the single buckets as input to the machine learning model comprises:
providing an identifier of a particular bucket as input to the machine learning model only once for the medical bill.

17. The computer-implemented method of claim 15, further comprising:
    applying the output of the machine learning model as input to one or more predetermined rules; and
    determining whether the medical bill should be reviewed by a human based on output of the one or more predetermined rules.

18. The computer-implemented method of claim 15, wherein:
    the attributes comprise at least one code, each code being either a procedure code or a diagnostic code; and
    the predetermined correspondence between the codes and the buckets is based on categories established by at least one health organization.

19. The computer-implemented method of claim 15, wherein:
    the attributes comprise procedure codes;
    the predetermined correspondence between the procedure codes and the buckets is based on categories established by the American Medical Association;
    the attributes comprise diagnostic codes; and
    the predetermined correspondence between the diagnostic codes and the buckets is based on categories established by the World Health Organization.

20. The computer-implemented method of claim 15, wherein:
    a first value of the binary numbers indicates an attribute of the medical bill was mapped to the corresponding bucket, and
    a second value of the binary numbers indicates no attribute of the medical bill was mapped to the corresponding bucket; and
    providing identifiers of the single buckets as input to a machine learning model comprises providing the vector of binary numbers as input to a machine learning model.

* * * * *